United States Patent
Webster

(10) Patent No.: US 11,541,385 B2
(45) Date of Patent: Jan. 3, 2023

(54) METHODS OF MEASURING HEMATOCRIT IN FLUIDIC CHANNELS INCLUDING CONDUCTIVITY SENSOR

(71) Applicant: QORVO US, INC., Greensboro, NC (US)

(72) Inventor: James Russell Webster, Minnetonka, MN (US)

(73) Assignee: Qorvo US, Inc., Greensboro, NC (US)

( * ) Notice: Subject to any disclaimer, the term of this patent is extended or adjusted under 35 U.S.C. 154(b) by 979 days.

(21) Appl. No.: 16/120,225

(22) Filed: Sep. 1, 2018

(65) Prior Publication Data

US 2020/0011825 A1    Jan. 9, 2020

Related U.S. Application Data

(60) Provisional application No. 62/694,621, filed on Jul. 6, 2018, provisional application No. 62/694,599, filed
(Continued)

(51) Int. Cl.
*B01L 3/00* (2006.01)
*G01F 1/58* (2006.01)
(Continued)

(52) U.S. Cl.
CPC .............. *B01L 3/502* (2013.01); *G01F 1/584* (2013.01); *G01N 27/08* (2013.01); *G01N 33/49* (2013.01);
(Continued)

(58) Field of Classification Search
CPC ................ B01L 3/502; B01L 2200/14; B01L 2300/0645; B01L 2200/16;
(Continued)

(56) References Cited

U.S. PATENT DOCUMENTS

| 4,547,735 A | 10/1985 | Kiesewetter et al. |
| 6,058,934 A | 5/2000 | Sullivan |

(Continued)

FOREIGN PATENT DOCUMENTS

| GB | 2501128 A | 10/2013 |
| WO | 2013/153406 A1 | 10/2013 |

(Continued)

OTHER PUBLICATIONS

Kim et al. "Improvement of the accuracy of continuous hematocrit measurement under various blood flow conditions" Appl. Phys. Lett. 104, 153508 (2014) (Year: 2014).*
(Continued)

*Primary Examiner* — Samuel P Siefke
*Assistant Examiner* — Quocan B Vo
(74) *Attorney, Agent, or Firm* — Haynes and Boone, LLP

(57) ABSTRACT

A device and a method of using the device for determining hematocrit in a whole blood sample. The device includes a first portion having an introducer, at least one fluid channel, a fluid actuator, and an analysis sensor and conductivity sensor disposed within the fluid channel. The second portion includes at least one well containing at least one material. The first portion and second portion are movable with respect to each other. The introducer is configured to transfer at least a portion of the material from the well in portion two into the fluid channel of portion one. The method includes measuring the resistance over substantially the entire portion of a whole blood sample and calculating an average hematocrit level of the whole blood sample based on the measured resistance.

20 Claims, 1 Drawing Sheet

Related U.S. Application Data on Jul. 6, 2018, provisional application No. 62/694,594, filed on Jul. 6, 2018.

(51) Int. Cl.
  *G01N 27/08* (2006.01)
  *G01N 33/49* (2006.01)

(52) U.S. Cl.
  CPC ... *B01L 2200/0605* (2013.01); *B01L 2200/14* (2013.01); *B01L 2200/16* (2013.01); *B01L 2300/0645* (2013.01); *B01L 2300/0663* (2013.01)

(58) Field of Classification Search
  CPC ..... B01L 2300/0663; B01L 2200/0605; B01L 3/502715; B01L 3/0293; B01L 2200/025; B01L 2300/0816; B01L 2300/0883; B01L 3/50855; B01L 2200/0684; B01L 2300/161; B01L 2300/0829; B01L 2300/0672; B01L 2300/044; B01L 2400/0487; B01L 3/5027; G01N 27/08; G01N 33/49; G01N 29/02; G01N 29/022; G01N 29/036; G01N 29/222; G01N 33/54366; G01N 2291/0255; G01N 2291/0256; G01N 2291/0426; G01N 33/4875; G01F 1/584
  See application file for complete search history.

(56) References Cited

U.S. PATENT DOCUMENTS

| | | | |
|---|---|---|---|
| 2001/0049148 A1 | 12/2001 | Wolk et al. | |
| 2008/0297169 A1 | 12/2008 | Greenquist et al. | |
| 2009/0084678 A1* | 4/2009 | Joshi | A61B 5/14865 204/403.14 |
| 2012/0258472 A1* | 10/2012 | Roy | G01N 35/1002 73/61.61 |
| 2012/0329144 A1 | 12/2012 | Kwak et al. | |
| 2014/0273265 A1 | 9/2014 | Feingold et al. | |
| 2016/0091506 A1 | 3/2016 | Webster | |
| 2016/0116444 A1 | 4/2016 | Webster et al. | |
| 2020/0011849 A1 | 1/2020 | Webster et al. | |

FOREIGN PATENT DOCUMENTS

| | | |
|---|---|---|
| WO | 2014/190295 A2 | 11/2014 |
| WO | 2016/049557 A1 | 3/2016 |

OTHER PUBLICATIONS

Kim et al. "Improvement of electrical blood hematocrit measurements under various plasma conditions using a novel hematocrit estimation parameter" Biosensors and Bioelectronics 35 (2012) 416-420 (Year: 2012).*

Rothe et al. "Continuous measurement of conductivity of biological fluids" Journal of Applied Physiology vol. 23, No. 6, Dec. 1967 (Year: 1967).*

Trebbels et al. "Capacitive on-line hematocrit sensor design based on Impedance Spectroscopy for use in hemodialysis machines" 31st Annual International Conference of the IEEE EMBS Minneapolis, Minnesota, USA, Sep. 2-6, 2009 (Year: 2009).*

Hbanov et al. "Electrochemical impedance spectroscopy of blood for sensitive detection of blood hematocrit, sedimentation and dielectric properties" Anal. Methods, 2017, 9, 3302-3313 (Year: 2017).*

Teodorczyk et al. "Hematocrit Compensation in Electrochemical Blood Glucose Monitoring Systems", J Diabetes Sci Technol vol. 6, Issue 3, May 2012 (Year: 2012).*

Jung et al. "Determination of hematocrit using on-line conductance cell" International Journal of Heat and Mass Transfer 55 (2012) 1836-1843 (Year: 2012).*

Burns et al., "An Integrated Nanoliter DNA Analysis Device", Science, vol. 282, Oct. 16, 1998, pp. 484-487.

International Search Report and Written Opinion for PCT Application No. PCT/US2019/039465 dated Sep. 5, 2019, 10 pages.

Sandberg et al., "Relation Between Blood Resistivity and Hematocrit in Fresh Human Fetal Blood", Pediatr. Res. 15, 1981, pp. 964-966.

Extended European Search Report dated Feb. 28, 2022 in related application EP 19 83 1195.3, 7 pages.

Extended European Search Report dated Feb. 28, 2022 in related application EP 19 83 1197.9, 7 pages.

\* cited by examiner

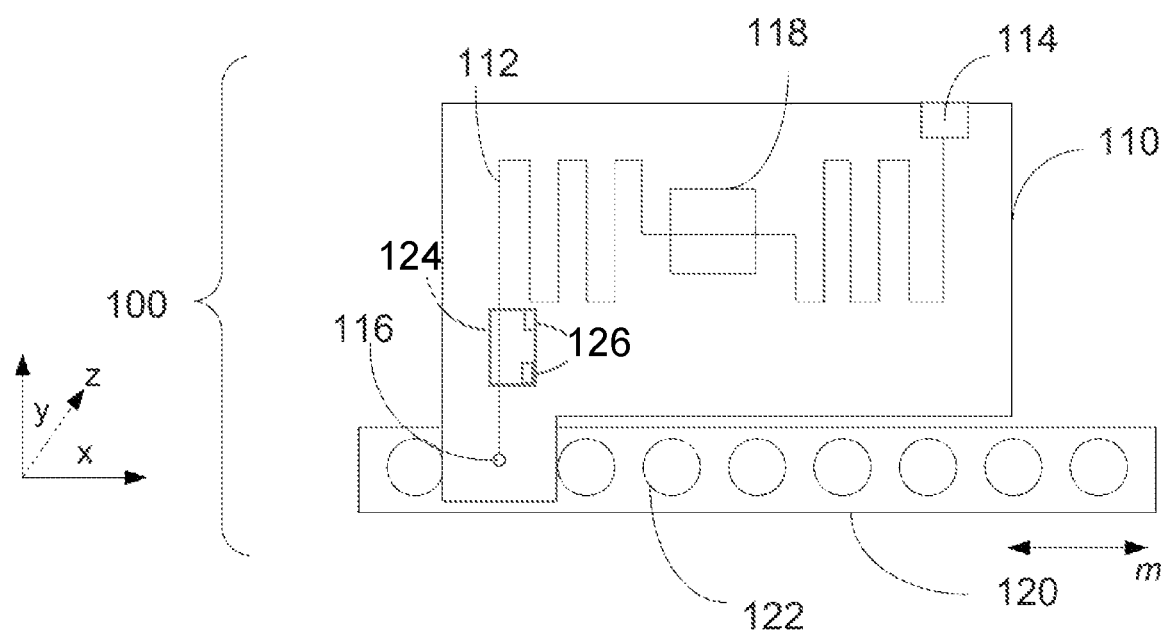

METHODS OF MEASURING HEMATOCRIT IN FLUIDIC CHANNELS INCLUDING CONDUCTIVITY SENSOR

RELATED APPLICATION

This application claims the benefit of U.S. Provisional Patent Application No. 62/694,594 filed on Jul. 6, 2018, U.S. Provisional Patent Application No. 62/694,599 filed on Jul. 6, 2018, and U.S. Provisional Patent Application No. 62/694,621 filed on Jul. 6, 2018, the disclosures of which are incorporated herein by reference thereto.

BACKGROUND

There are numerous instruments and measurement techniques for diagnostic testing of materials related to medical, veterinary medical, environmental, biohazard, bioterrorism, agricultural commodity, and food safety. Diagnostic testing traditionally requires long response times to obtain meaningful data, involves expensive remote or cumbersome laboratory equipment, requires large sample size, utilizes multiple reagents, demands highly trained users, and can involve significant direct and indirect costs. For example, in both the human and veterinary diagnostic markets, most tests require that a sample be collected from a patient and then sent to a laboratory, where the results are not available for several hours or days. As a result, the caregiver must wait to treat the patient.

Point of use (or point of care when discussing human or veterinary medicine) solutions for diagnostic testing and analysis, although capable of solving most of the noted drawbacks, remain somewhat limited. Even some of the point of use solutions that are available are limited in sensitivity and reproducibility compared to in laboratory testing. There is also often significant direct costs to a user as there can be separate systems for each point of use test that is available.

SUMMARY

Disclosed herein are devices that include a first portion, the first portion including at least one fluid channel; a fluid actuator; an analysis sensor disposed within the fluid channel; a conductivity sensor comprising two electrodes that are no more than 10 millimeters away from each other disposed within the fluid channel; and an introducer; a second portion, the second portion including at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel.

Also disclosed are methods of determining hematocrit in a whole blood sample utilizing a system, the system including a first portion, the first portion including at least one fluid channel; a fluid actuator; an analysis sensor disposed within the fluid channel; a conductivity sensor including two electrodes located no more than 10 mm away from each other and disposed within the fluid channel; and an introducer; a second portion, the second portion including at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel, the method including measuring the resistance over substantially the entire portion of a whole blood sample; and calculating an average hematocrit level of the whole blood sample based on the measured resistance.

Also disclosed are methods of determining hematocrit in a whole blood sample utilizing a system, the system including a first portion, the first portion including at least one fluid channel; a fluid actuator; an analysis sensor disposed within the fluid channel; a conductivity sensor including two electrodes located no more than 10 mm away from each other and disposed within the fluid channel; and an introducer; a second portion, the second portion including at least one well, the well containing at least one material, wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel, the method including measuring the resistance over at least 75% of a whole blood sample; and calculating an average hematocrit level of the whole blood sample based on the measured resistance.

These and various other features will be apparent from a reading of the following detailed description and related drawings.

BRIEF DESCRIPTION OF THE DRAWINGS

FIG. 1 is a schematic diagram illustrating an illustrative sensor assembly.

DETAILED DESCRIPTION

In the following detailed description several specific embodiments of compounds, compositions, products and methods are disclosed. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a composition, product, method or the like, means that the components of the composition, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

Any direction referred to herein, such as "top," "bottom," "left," "right," "upper," "lower," and other directions and orientations are described herein for clarity in reference to the figures and are not to be limiting of an actual device or system or use of the device or system. Devices or systems as described herein may be used in a number of directions and orientations.

Disclosed devices can be utilized to measure hematocrit in a whole blood sample. Disclosed devices include a conductivity sensor that can determine the conductivity of at least a portion of a whole blood sample in a fluidic channel of a device. Because the concentration of ions in blood is regulated and maintained consistent by the body, the resistivity of whole blood is a reasonably accurate measure of the percentage of blood cells present in the whole blood (hematocrit). Sandberg et. al. (Pediatr. Res. 15:964-966(1981)) describes the relationship between blood resistivity and hematocrit in fetal blood sample. A good fit was found using either an exponential relationship or the Maxwell Frick equation. When measuring analytes in whole blood samples, it is usually necessary to adjust the result to reflect the concentration of the analyte in the plasma of that sample. The extra volume occupied by the blood cells, typically reduces the measured result in proportion to the hematocrit.

Disclosed herein is an assembly. In some embodiments, assemblies can include a first portion and a second portion. The first and second portions can be configured to be assembled together to form an assembly. The first and second portions can be assembled together by a manufacturer, an assembler, an end-user, or any combination thereof. The assembly of the two portions can be facilitated by the shape of the two portions, components of at least one of the two portions that are designed to facilitate assembly, or some combination thereof. The two portions can be made of the same material(s) or different materials. In some embodiments the first portion and the second portion can be made of different materials, which because of the different purposes of the two portions, may be useful. The two portions of the assembly can be manufactured separately, in the same or different facilities; and/or can be packaged and/or sold separately or together.

At least one of the first and second portions is moveable with respect to the other. This implies that after the first and second portion are assembled to form the assembly, one portion is moveable with respect to the other. The portion that is moveable with respect to the other can be moveable in one or more directions or dimensions. Movement of one portion with respect to the other may offer advantages in that wells in the second portion (discussed below) can be randomly accessed by the first portion. The ability to randomly access the wells in the second portion can allow a large breadth of protocols to be accomplished without altering the configuration of the assembly itself. Other possible advantages provided by the movability of one portion with respect to the other portion are discussed throughout this disclosure.

FIG. 1 illustrates an illustrative embodiment of an assembly. This illustrative assembly 100 includes a first portion 110 and a second portion 120. This particular illustrative assembly 100 is configured to be assembled in a way that positions the second portion 120 below the first portion 110 in the z direction. In some embodiments, the second portion 120 is moveable with respect to the first portion 110. The second portion being moveable with respect to the first portion can imply that the second portion can move in at least one dimension (x, y, or z) with respect to the first portion, which is stationary. In some embodiments, the second portion can move along a straight line with respect to the first portion (for example, along the x dimension). The embodiment depicted in FIG. 1 shows such movement, with the second portion 120 moving in the x direction (as indicated by the arrow designated m). In some embodiments, the second portion can move along a straight line with respect to the first portion (for example along the x dimension) and can move up and down with respect to the first portion (for example along the z dimension). Such movement could be seen in the assembly 100 if the second portion 120 also moved in the z dimension.

First Portion

The first portion can include at least one fluidic pathway, a fluid actuator, and an introducer. Fluidic pathways can also be described as including a fluid channel. The illustrative first portion 110 illustrated in FIG. 1 includes a fluid channel 112, a fluid actuator 114, and an introducer 116. Generally, the fluid channel 112, the fluid actuator 114, and the introducer 116 are in fluid communication with one another. It can also be described that the fluid actuator 114, the introducer 116, and the fluid channel 112 are within, on, or are part of the fluidic pathway.

The fluidic pathway can have various configurations, and the examples depicted herein serve only as illustrative configurations. In some embodiments, the fluidic pathway does not include portions of the device that obtain the sample. In some embodiments, the fluidic pathway begins after a sample is contained in a well of the second portion. The fluidic pathway can be described as a transit path for fluids in the assembly. The fluidic pathway need not be fluidly connected at all times. For example, the fluidic pathway can include a portion of the device that can be (based may be moved into or out of the fluid pathway, by for example moving one portion with respect to another portion. The fluidic pathway can also be described as including any portion of the device accessible by the introducer, any portion of the device fluidly connected with any portion of the device accessible by the introducer, or some combination thereof. The fluidic pathway need not include only an actual volume that is connected. In some embodiments, a fluidic pathway can be entirely housed on a first portion, entirely housed on a second portion, or at least one portion of a fluidic pathway can exist on a first and at least one portion of a fluidic pathway can exist on a second portion. In some embodiments, a fluidic pathway can be one that is connected at all times and in some embodiments, one or more than one portion of a fluidic pathway can be at some times disconnected from the remainder of the fluidic pathway. In some embodiments, a fluidic pathway can include a fluid channel. In some embodiments, such a fluid channel can be a volume that is connected at all times. In some embodiments, such a fluid channel can be entirely housed on the first portion of an assembly. In some embodiments, such a fluid channel can be entirely housed on the first portion of an assembly can be a volume that is statically connected at all times. A fluid channel can refer to a physical channel on a first portion of an assembly.

In some embodiments, the fluidic pathway does not include valves. In some embodiments, the fluid channel does not include valves. In some embodiments, fluid can flow in either direction in the fluidic pathway (or in the fluid channel) even though there are no valves. Bi-directional flow is possible, even though there may be no valves in the fluidic pathway (or the fluid channel) because of the ability to randomly access wells (for example an empty well) in the second portion. More specifically, two directional flow can be accomplished by depositing liquid (in some embodiments all the liquid) in the fluidic pathway (or the fluid channel) in an empty well on the second portion by flowing the fluid in a first direction and then retrieving that liquid from that well and directing it in the fluidic pathway by flowing the fluid in a second direction (opposite to the first direction). Accomplishing two way flow without the use of any valves can make disclosed assemblies more cost effective to manufacture and less prone to issues that may accompany the use of valves.

Fluidic pathways (and therefore fluid channels that are part of a fluidic pathway) can have access to a sample introduction pathway as well. The sample introduction pathway and the fluidic pathway need not be entirely located on or in the same portion. The sample introduction pathway can include one or more than one component that can function to get a sample into a well. The sample introduction pathway can be described as a transit path for the sample before it is in a well. The sample introduction pathway need not be fluidly connected at all times. For example, the sample introduction pathway can include a portion of the device that can be (based on for example movement of one portion with respect to the other portion) moved into or out of the sample introduction pathway.

The sample introduction pathway can include, for example a sample introduction chamber and one or more than one component to get a sample from the sample introduction chamber to a well (on the second portion, discussed below). In some embodiments the sample introduction pathway can include one or more than one irreversible valve. A valve or valves that may be in the sample introduction pathway can also be described as not including moving parts. In some embodiments the sample introduction chamber can be located on or in the first portion. The sample introduction pathway can for example include a valve(s), a filter(s), or some combination thereof. In some embodiments the sample introduction pathway can utilize the introducer portion of the first portion. In some embodiments the sample can be moved from a sample introduction chamber to a sample well on the second portion.

In some embodiments, a sample introduction pathway can be configured to introduce sample directly into a fluidic pathway or a fluid channel that is part of a fluidic pathway. In such embodiments, the sample introduction pathway would be configured to deposit a sample into the fluidic pathway without first depositing it into a sample well. Such configurations could be especially useful or applicable to instances where the sample size is relatively small. In some embodiments, such configurations could be utilized for sample sizes of not greater than 100 µL, for example. An example of such a sample could include a quantity of blood obtained via a finger prick.

FIG. 1 shows a fluid channel 112 that is part of the fluidic pathway. The fluid channel 112 can be formed (i.e., top, bottom and sides) from more than one component or piece of the first portion. In some embodiments, the fluid channel 112 does not contain any fluid valves. Illustrative fluid channels can be described by their volumes, either by their total volumes or by the volume both before and after the analysis sensor. In some embodiments, illustrative fluid channels can have volumes of 10 µL to 1000 µL in the region before the analysis sensor and 10 µL to 1000 µL in the region after the analysis sensor. In some embodiments, illustrative fluid channels can have volumes of 50 µL to 250 µL in the region before the analysis sensor and 50 µL to 250 µL in the region after the analysis sensor. In some embodiments, illustrative fluid channels can have volumes of 75 µL to 200 µL in the region before the analysis sensor and 75 µL to 200 µL in the region after the analysis sensor. In some embodiments, illustrative fluid channels can have volumes of 100 µL to 175 µL in the region before the analysis sensor and 100 µL to 175 µL in the region after the analysis sensor. It should also be understood that the volumes before and after the analysis sensor need not be the same.

The first portion also includes a fluid actuator 114. Although fluid actuator 114 is depicted as being at one end of the fluid channel 112, it should be understood that a fluid actuator could be located at any point along the fluid channel 112, could be located at multiple points along the fluid channel 112, and/or could have multiple components at multiple points along the fluid channel 112. The fluid actuator 114 functions to move fluid along the fluid channel 112. It can also be described that the fluid actuator 114 functions to move fluid along, into, out of, within (or any combination thereof) the fluid channel 112.

The fluid actuator 114 can be as simple as a port or as complex as a pump or diaphragm. In some embodiments, the fluid actuator 114 can be a port at the end of the fluid channel 112 (for example such as that depicted in FIG. 1) that is in fluid communication with a pump located external to the first portion. In some embodiments, the fluid actuator 114 is a port that is in fluid communication with a pump that is located on or within an external instrument that is configured to control and/or manipulate the sensor assembly. In some embodiments, the fluid actuator 114 can be a port that is in fluid communication with an entire fluidic control system. Illustrative fluidic control systems can include a pump(s), diaphragm(s), valve(s), further fluid channel(s), reservoir(s), or some combination thereof. In some embodiments, at least portions of the illustrative fluidic control system can be located on or within an external instrument, the first portion of the sensor assembly, the second portion of the sensor assembly, or some combination thereof. In some embodiments, the fluid actuator 114 can include a diaphragm that is in fluid communication with some portion of a fluidic control system.

The first portion also includes an introducer 116. The introducer 116 is on, within, or fluidly attached to the fluid channel 112 and functions to access the wells of the second portion (discussed below). The function of the introducer 116 can also be described as being configured to obtain at least a portion of the contents of at least one well on the second portion. The introducer 116 can be described as being able to both puncture sealed wells of the second portion and access and obtain at least a portion of the material in the well. The introducer 116 can be actuated by an external instrument in order to access the wells. Such actuation can include movement in one or more than one dimension. For example, in the example depicted in FIG. 1, movement of the introducer 116 in the z direction could afford access to at least one well on the second portion.

In some embodiments, the introducer 116 can also be configured to introduce air into a well it has accessed. This may allow the introducer 116 to more reliably obtain material from the wells. This optional function of the introducer 116 can be realized by the particular design of the tip of the introducer, by puncturing the seal to the well at two (instead of one) points simultaneously, at different times in a specified order, or by combinations thereof. In some embodiments, the introducer 116 can be similar in shape and configuration to a pipette tip.

The introducer 116 can also be configured to both extract material from a well of the second portion and introduce material into a well of the second portion. In such embodiments, the external instrument, in some embodiments through control of a pump for example, can control whether the introducer 116 is extracting or introducing material from or into the well. Introducing material into a well can allow for storage of materials, while not requiring a user to have concerns about liquids spilling out of a used sensor assembly. Introducing material into a well can also provide a method of mixing. Introducing material into a well can also provide a method of storing an intermediate composition while another step of a protocol is being carried out.

In some embodiments, the first portion 110 can also include an analysis sensor 118. An analysis sensor in a first portion can be any type of sensor, for example it could be an optical sensor (using for example chemiluminescence or fluorescence), an electrochemical sensor, or a resonant sensor. In some embodiments, the analysis sensor 118 can include at least one resonator sensor. Examples of such sensors can include bulk acoustic wave (BAW) sensors and thin film bulk acoustic resonator (TFBAR) sensor. Both BAW and TFBAR sensors include a piezoelectric layer, or piezoelectric substrate, and input and output transducer. Both BAW and TFBAR sensors are small sensors making the technology particularly suitable for use in handheld or portable devices.

In some embodiments, the analysis sensor 118 can be within or form part of the fluidic pathway. More specifically, in some embodiments, the analysis sensor 118 can be within or form part of the fluid channel. For example, a portion of the fluidic pathway can be configured to exist within or form part of the fluidic pathway so that fluid in the fluidic pathway flows over the analysis sensor. In some embodiments, the fluid in the fluidic pathway can travel completely around the sensor, and in other embodiments, the fluid in the fluidic pathway can travel around less than all surfaces of the analysis sensor. In some embodiments, the fluid in the fluidic pathway can travel across the active region of the analysis sensor. In some embodiments, the fluid in the fluidic pathway can flow over the piezoelectric layer of the analysis sensor, which is coated with binding sites for an analyte of interest.

The analysis sensor can be any type of sensor. In some embodiments the analysis sensor can be an optical sensor (for example a chemiluminescent sensor or a fluorescent sensor) or a resonant sensor, for example. In some embodiments the analysis sensor can be a resonant sensor, such as a BAW sensor.

Disclosed devices include a conductivity 124 sensor disposed within the fluidic channel. The conductivity sensor can generally include at least two electrodes 126. In some embodiments, the electrodes are made of a material that will not be reactive with the fluid (e.g., sample, reagents, or sample and reagents in combination) that will be located within the fluidic channel. In some embodiments, the electrodes can be made of a substantially chemically inert material. In some embodiments, the electrodes can be made of gold for example.

The at least two electrodes 126 can have the voltage and current characteristics configured in order to measure the resistance of the fluid within the fluidic channel. The at least two electrodes can be employed with alternating current (AC), direct current (DC), or a combination thereof. In some embodiments, AC current can be utilized as it will prevent or at least minimize hydrolysis at the surface of the electrodes. In some embodiments, relatively low current are utilized in order to avoid substantial joule heating of the fluid within the fluidic channel The conductivity sensor 124 can be in communication, for example electrical communication, with a processor that can obtain signals from the sensor and utilize the signal for various purposes. Additionally, or alternatively, the conductivity sensor 124 can be controlled by a processor, e.g., the processor can activate the conductivity sensor at various times, for various lengths of time, or combinations thereof.

The conductivity sensor can be located upstream of the analysis sensor or downstream of the analysis sensor. In some embodiments, the at least two electrodes can be separated by a relatively short distance. For example, the at least two electrodes can be separated by no more than 10 millimeters (mm), no more than 3 mm, or even no more than 1 mm.

In anti-coagulated whole blood samples, blood cells can settle. Therefore a sample can have localized regions of higher or lower than average hematocrit levels due to settling. Measuring hematocrit with a conductivity sensor 124 in a small localized region could give an inaccurate result if cells have settled near the sensor or away from the sensor. Disclosed methods measure the conductivity over substantially the entire portion of a whole blood sample. Therefore it is advantageous to utilize a sensor that can interrogate a large percentage of the sample to accurately estimate the hematocrit level. In some embodiments, substantially the entire portion of a whole blood sample can refer to at least 75% of a whole blood sample, at least 85% of a whole blood sample, or even at least 95% of a whole blood sample. The hematocrit level of the blood sample can then be determined by calculating the average hematocrit level of the blood sample.

The conductivity of the sample can be monitored on an ongoing basis at an interval that can be determined by the processor, the speed of electronics being used in the system, the level of accuracy necessary for the analysis, or any combination thereof. The results of monitoring the conductivity can be a curve of resistance (or 1/conductivity) versus time. The hematocrit can then be calculated using known methods by determining the average conductivity by integrating the area under the curve or by determining the hematocrit values over the curve and then determining the average hematocrit value.

Disclosed methods can be advantageous because they compensate for settling of the whole blood sample, variability in the hematocrit levels in the sample, or any combination thereof. Furthermore, disclosed methods can be advantageous because the hematocrit of the actual portion of the sample being analyzed is being measured, further eliminating problems due to variability in whole blood samples. This can be advantageous because the hematocrit level can be utilized to correct the analysis done by the analysis sensor, so measuring on the same portion of the sample reduces error due to variability in the whole blood sample.

Second Portion

Disclosed assemblies also include a second portion. The second portion can include at least one well. FIG. 1 depicts an illustrative second portion 120 that includes a plurality of wells 122. Disclosed second portions of the assembly can include any number of wells. In some embodiments, a second portion can include at least one (1), at least three (3), or at least five (5) wells. In some embodiments, a second portion can include nine (9) wells with one being a sample well.

The wells within a second portion can be configured to contain the same or different volumes. In some embodiments, the wells can be of a size to contain at least 10 µL. In some embodiments, the wells can be of a size to contain from 50 µL to 150 µL, for example. In some embodiments, the wells can be of a size to contain about 100 µL for example. In some embodiments, the wells can have a total volume that is more than the quantity which they are designed to hold. For example, a well can have a total volume that is 200 µL in order to house a volume of 100 µL. The wells can have various configurations, including for example corners, flat bottoms, and round bottoms. The wells can have various shapes, for example, they can be cylindrical, or spherical, hexagonal, or otherwise. The wells can be present in any configuration, linear (as depicted in FIG. 1, circular, or otherwise).

Wells within a second portion can contain various materials or can be empty. In some embodiments, a second portion can include at least one well that is empty. In some embodiments a second portion can include at least one sample well. The sample well can generally be empty before the assembly is used. The sample well in such embodiments can be utilized to hold at least a portion of the sample transferred from a sample introduction chamber via the sample introduction pathway. In some embodiments, the sample well can include one or more than one materials, which the sample will be combined with upon introduction into the sample well.

Materials contained within wells can be liquid or solid. Materials contained within wells can also be referred to as reagents, diluents, wash solutions, buffer solutions, or other such terms. In some embodiments, material within a well can be a single material that is a liquid at room temperature, a solution containing more than one material, or a dispersion containing one material dispersed in another. In some embodiments, material within a well can be a solid. The material within an individual well can be independently selected with respect to materials in other wells. In some embodiments, the materials within a well are selected to carry out a particular testing protocol.

The second portion can also include a seal. Generally, the seal functions to contain the materials within the wells. In some embodiments, the seal can be a unitary element, while in some embodiments, the seal can be made up of more than one element. For example, with reference to FIG. 1, in some embodiments, a single element could cover all of the wells 122. While in some other embodiments, each well 122 could be covered by an individual element, with all of the elements making up the seal. The seal can be made of any material that can function to maintain the contents of the wells within the wells, but also allow the introducer access to the materials in the wells. Illustrative materials can include, for example, a foil, such as a metallic foil which can be sealed to the second portion (or portions thereof) via an adhesive or heat sealing; plastic films; or other such materials. In some embodiments, the seal is made of a metallic foil and covers the entirety of the second portion.

The second portion can also include a way of introducing a sample either directly or indirectly from a user. For example, in some embodiments, a second portion can include an empty well, whose seal can be pierced (if it is sealed) by a portion of a disclosed assembly or a user to introduce a sample to be tested by the sensor assembly. This well can be referred to as the sample well. In some embodiments, the sample well is not covered by the seal. In some embodiments where the sample is introduced directly to the second portion by a user it can be added to the sample well via a syringe, a pipette, or other similar instruments. In some embodiments, the sample can be added to a sample well via, for example a sample introduction pathway.

USES

The devices, systems, and methods described herein may be employed to detect a target analyte in a whole blood sample and calculate the hematocrit levels in the sample. Non-limiting examples of target analytes include nucleic acids, proteins, peptides, antibodies, enzymes, carbohydrates, chemical compounds, or infectious species such as bacteria, fungi, protozoa, viruses, pesticides and the like. In certain applications, the target analyte is capable of binding more than one molecular recognition component.

Thus, embodiments of METHODS OF MEASURING HEMATOCRIT IN FLUIDIC CHANNELS INCLUDING CONDUCTIVITY SENSOR are disclosed. The implementations described above and other implementations are within the scope of the following claims. One skilled in the art will appreciate that the present disclosure can be practiced with embodiments other than those disclosed. The disclosed embodiments are presented for purposes of illustration and not limitation.

What is claimed is:

1. A method of determining hematocrit in a whole blood sample utilizing a system, the system comprising:
   a first portion, the first portion comprising:
      at least one fluid channel;
      a fluid actuator;
      an analysis sensor disposed within the fluid channel;
      a conductivity sensor comprising only two electrodes located no more than 10 mm away from each other and disposed within the fluid channel; and
      an introducer;
   a second portion, the second portion comprising:
      at least one well, the well containing at least one material,
   wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel,
   the method comprising:
   measuring the resistance over substantially the entire portion of a whole blood sample wherein the whole blood sample comprises no more than 100 µL of blood; and
   calculating the hematocrit level of the whole blood sample based on the measured resistance.

2. The method according to claim 1, wherein substantially the entire portion of a whole blood sample is at least 75% of the whole blood sample.

3. The method according to claim 1, wherein substantially the entire portion of a whole blood sample is at least 85% of a whole blood sample.

4. The method according to claim 1, wherein substantially the entire portion of a whole blood sample is at least 95% of a whole blood sample.

5. The method according to claim 1, wherein the hematocrit level of the whole blood sample is calculated by integrating the area under a curve of time versus the measured resistance.

6. The method according to claim 1, wherein the two electrodes are powered using an alternating current (AC).

7. The method according to claim 1, wherein the determined hematocrit level is an average hematocrit level of substantially the entire whole blood sample.

8. The method according to claim 1, wherein the two electrodes are located no more than 3 mm away from each other.

9. The method according to claim 1, wherein the two electrodes are located no more than 1 mm away from each other.

10. The method according to claim 1, wherein the analysis sensor is a resonator sensor.

11. The method according to claim 10, wherein the resonator sensor is a bulk acoustic wave (BAW) sensor.

12. The method of claim 1, wherein the two electrodes comprise a substantially chemically inert material.

13. A method of determining hematocrit in a whole blood sample utilizing a system, the system comprising:
a first portion, the first portion comprising:
at least one fluid channel;
a fluid actuator;
an analysis sensor disposed within the fluid channel;
a conductivity sensor comprising only two electrodes located no more than 10 mm away from each other and disposed within the fluid channel; and
an introducer;
a second portion, the second portion comprising:
at least one well, the well containing at least one material,
wherein one of the first or second portion is moveable with respect to the other, wherein the introducer is configured to obtain at least a portion of the material from the at least one well and deliver it to the fluid channel, and wherein the fluid actuator is configured to move at least a portion of the material in the fluid channel,
the method comprising:
measuring the resistance over at least 75% of a whole blood sample, wherein the whole blood sample comprises no more than 100 μL of blood;
calculating an average hematocrit level of the whole blood sample based on the measured resistance.

14. The method according to claim 13, wherein substantially the entire portion of a whole blood sample is at least 95% of a whole blood sample.

15. The method according to claim 13, wherein the two electrodes are powered using an alternating current (AC).

16. The method according to claim 13, wherein the two electrodes are located no more than 3 mm away from each other.

17. The method according to claim 13, wherein the two electrodes are located no more than 1 mm away from each other.

18. The method according to claim 13, wherein the analysis sensor is a resonator sensor.

19. The method according to claim 18, wherein the resonator sensor is a bulk acoustic wave (BAW) sensor.

20. The method of claim 13, wherein the two electrodes comprise a substantially chemically inert material.

* * * * *